United States Patent
MacNicol

(10) Patent No.: US 7,030,224 B2
(45) Date of Patent: Apr. 18, 2006

(54) HUMAN CYTOPLASMIC POLYADENYLATION ELEMENT BINDING PROTEIN AND USES THEREOF

(75) Inventor: Angus M. MacNicol, Little Rock, AR (US)

(73) Assignee: The Board of Trustees of the University of Arkansas System, Little Rock, AR (US)

( * ) Notice: Subject to any disclaimer, the term of this patent is extended or adjusted under 35 U.S.C. 154(b) by 477 days.

(21) Appl. No.: 10/349,852

(22) Filed: Jan. 23, 2003

(65) Prior Publication Data
US 2004/0076970 A1   Apr. 22, 2004

Related U.S. Application Data

(60) Provisional application No. 60/351,121, filed on Jan. 23, 2002.

(51) Int. Cl.
| | |
|---|---|
| A61K 38/18 | (2006.01) |
| A61K 38/16 | (2006.01) |
| C12N 15/12 | (2006.01) |
| C12Q 1/68 | (2006.01) |
| C12Q 1/48 | (2006.01) |

(52) U.S. Cl. .................. 530/358; 435/69.2; 435/6; 435/15

(58) Field of Classification Search ............... 530/358; 435/69.2, 6, 15
See application file for complete search history.

(56) References Cited

OTHER PUBLICATIONS

Hake et al., "CPEB is a specificity factor that mediates cytoplasmic polyadenylation during Xenopus oocyte maturation," Cell 79:617-627, 1994(Result 1), PIR 79 database search, printed on Aug. 8, 2005.*
Helix Research Institute, EP 1074617 A2, claim 8, SEQ ID No.: 15,235 (Result 4), Geneseq database search, printed on Aug. 8, 2005.*
Gebauer et al., "Mouse cytoplasmic polyadenylation element binding protein: An evolutionarily conserved protein that interacts with the cytoplasmic polyadenylation elements of c-mos mRNA," Proc Natl Acad Sci USA 93:14602-14607, 1996 (Result 3), (cont'd.) UniProt/TrEMBL database search, printed on Aug. 8, 2005.*
Welk et al., "Identification and characterization of the gene encoding human cytoplasmic polyadenylation element-binding protein," Gene 263: 113-120, 2001 (Result 4); UniProt/TrEMBL database search, printed on Aug. 8, 2005.*
UniProt/TrEMBL (Translated EMBL Nucleotide Sequence Data Library), Record No. Q9H8V5, GenBank Accession No. BAB14496, last sequence update Mar. 1, 2001 (Result 6), UniProt/TrEMBL database search, printed on Aug. 8, 2005.*

* cited by examiner

*Primary Examiner*—Robert A. Wax
*Assistant Examiner*—Rosanne Kosson
(74) *Attorney, Agent, or Firm*—Benjamin Aaron Adler

(57) ABSTRACT

The present invention provides genomic and cDNA encoding human cytoplasmic polyadenylation element binding protein, expression vectors comprising human cytoplasmic polyadenylation element binding protein cDNA and host cells that contain the expression vectors. Also provided are recombinant human cytoplasmic polyadenylation element binding protein and polypeptides derived thereof.

2 Claims, 11 Drawing Sheets

```
                                                 *50
TAAATGTCAATATGTTTTCTGGCATTGCTACTTCAACATCGTCTTCCATGT
                                                 100
CTGGCACTGGTTTGGAGCACTCATCTCTATCAGATTGTCTTCTGCTAATT
                                                 150
CCTCTGGTATGTTAACTCTTGGATTTCTCCAAGGTCCATGTCTTGGAAAT
                                                 200
CTTCACTCCCAACCTTTTTTGTCATATCTACAGTTTCTTTCATGATTTC
                                                 250
CTGTATTGGCTCTGTGGTAAATCTGTGAAGTCATGTACAACATCTGGAAA
                                                 300
CAGTTTTTTTAAGCAGGAATTTATTATTTTGGGCATGATGGCTTTCATGG
                                                 350
ATTTTTCTGTAACAATGATGGCATTGTCACTGGAAGAAGAAGCAGGAAGG
                  M  A  L  S  L  E  E  E  A  G  R
                                                 400
ATAAAAGATTGCTGGGACAACCAGGAAGCACCTGCTCTCTCCACGTGTAG
 I  K  D  C  W  D  N  Q  E  A  P  A  L  S  T  C  S>
                                                 450
TAATGCCAATATCTTTCGAAGGATAAATGCCATATTGGATAATTCTCTGG
 N  A  N  I  F  R  R  I  N  A  I  L  D  N  S  L
```

```
                                                             *50
TAATGTCAATATGTTTTCTGGCATTGCTACTTCAACATCGTCTTCCATGT

100
CTGGCACTGGTTTGGAGCACTCATCTCTATCAGATTGTCTTCTGCTAATT

150
CCTCTGGTATGTTAACTCTTGGATTTCTCCAAGGTCCATGTCTTGGAAAT

200
CTTCACTCCCAACCTTTTTTTGTCATATCTACAGTTTCTTTCATGATTTC

250
CTGTATTGGCTCTGTGGTAAATCTGTGAAGTCATGTACAACATCTGGAAA

300
CAGTTTTTTTAAGCAGGAATTTATTATTTTGGGCATGATGGCTTTCATGG

▽                      350
ATTTTTCTGTAACAATGATGGCATTGTCACTGGAAGAAGAAGCAGGAAGG
              M   A   L   S   L   E   E   E   A   G   R

400
ATAAAGATTGCTGGGACAACCAGGAAGCACCTGCTCTCTCCACGTGTAG
  I   K   D   C   W   D   N   Q   E   A   P   A   L   S   T   C   S>

450
TAATGCCAATATCTTTCGAAGGATAAATGCCATATTGGATAATTCTCTGG
   N   A   N   I   F   R   R   I   N   A   I   L   D   N   S   L
```

Fig. 1A

```
                                               500
ATTTCAGTAGAGTCTGCACTACACCTATAAACCGAGGAATTCATGATCAT
 D  F  S  R  V  C  T  T  P  I  N  R  G  I  H  D  H> hCPEB (short)    550
         ▼
TTGCCAGACTTCCAGGACTCTGAAGAAACAGTTACAAGCAGGATGCTTTT
 L  P  D  F  Q  D  S  E  E  T  V  T  S  R  M  L  F 600
CCCAACCTCTGCGCAAGAATCTTCCCGTGGCCTCCCAGATGCAAATGACT
 P  T  S  A  Q  E  S  S  R  G  L  P  D  A  N  D>

650
TGTGCCTTGGCCTGCAGTCCCTCAGTCTGACAGGCTGGGACCGACCCTGG
 L  C  L  G  L  Q  S  L  S  L  T  G  W  D  R  P  W

▽        700
AGCACCCAGGACTCAGATTCCTCAGCCCAGAGCAGCACACACTCGGTACT
 S  T  Q  D  S  D  S  S  A  Q  S  S  T  H  S  V  L>

750
GAGCATGCTCCATAACCCACTGGGAAATGTCCTAGGAAAACCCCCCTTGA
 S  M  L  M  N  P  L  G  N  V  L  G  K  P  P  L

800
GCTTCCTGCCTC TGGATCC CCTTGGGTCTGACTTGGTGGACAAGTTTCCA
 S  F  L  P  L  D  P  L  G  S  D  L  V  D  K  P  P>
```

Fig. 1B

```
                                                           850
GCACCCTCAGTTAGAGGATCACGCCTGGACACCCGGCCCATCCTGGACTC
 A  P  S  V  R  G  S  R  L  D (T) R  P  I  L  D (S)

900
TCGATCTAGCAGCCCCTCTGACTCAGACACCAGTGGCTTCAGCTCTGGAT
 R  S  S  S  P  S  D  S  D  T  S  G  F  S  S  G>

▽                            950
CAGATCATCTCTCAGATTTGATTTCAAGCCTTCGCATTTCTCCACCTCTG
 S  D  H  L  S  D  L  I  S  S  L  R  I  S  P  P  L

1000
CCCTTCCTGTCTCTGTCAGGGGGTGGTCCCAGAGACCCTTTAAAGATGGG
  P  F  L  S  L  S  G  G  G  P  R  D  P  L  K  M  G>

1050
GGTAGGGTCTCGGATGGACCAAGAGCAAGCTGCTCTTGCTGCAGTCACTC
  V  G  S  R  M  D  Q  E  Q  A  A  L  A  A  V  T

1100
CCTCCCCAACCAGTGCTTCAAAGAGATGGCCAGGAGCTTCTGTGTGGCCA
 P  S  P  T  S  A  S  K  R  W  P  G  A  S  V  W  P>

1150
TCCTGGGACCTCCTCGAAGCTCCCAAAGACCCCTTCAGCATAGAGAGA
  S  W  D  L  L  E  A  P  K  D  P  F  S  I  E  R  E
```

Fig. 1C

```
                               ▽                              1200
GGCCAGGCTGCACCGACAAGCTGCAGCTGTGAATGAAGCCACCTGTACCT
  A   R   L   H   R   Q   A   A   A   V   N   E   A   T   C   T>

RRM1 ↰        1250
GGAGTGGCCAGCTTCCTCCCCGGAACTATAAGAACCCCATCTACTCTTGC
  W   S   G   Q   L   P   P   R   N   Y   K   N   P   I   Y   S   C

▽                1300
AAGGTGTTTCTAGGAGGTGTTCCTTGGGATATTACAGAAGCTGGATTAGT
  K   V   F   L   G   G   V   P   W   D   I   T   E   A   G   L   V>

1350
TAACACCTTCCGTGTTTTTTGGCTCTTTGAGTGTGGAGTGGCCTGGTAAGG
  N   T   F   R   V   F   G   S   L   S   V   E   W   P   G   K

▽  1400
ATGGCAAGCATCCCCGGTGTCCTCCCAAAGGTAATATGCCTAAAGGGTAT
  D   G   K   H   P   R   C   P   P   K   G   N   M   P   K   G   Y>

1450
GTGTATCTGGTCTTCGAACTAGAGAAGTCTGTCCGATCCTTGCTTCAGGC
  V   Y   L   V   F   E   L   E   K   S   V   R   S   L   L   Q   A

1500
TTGCTCTCATGACCCGCTGAGCCCAGATGGCCTGAGTGAATATTATTTCA
  C   S   H   D   P   L   S   P   D   G   L   S   E   Y   Y   F>
```

Fig. 1D

```
                    ←                              ▽                  1550
                AGATGTCCAGCCGAAGGATGCGCTGCAAGGAGGTGCAGGTGATCCCTGG
                 K  M  S  S  R  R  M  R  C  K  E  V  Q  V  T  P  W

1600
                GTATTAGCCGACAGTAACTTTGTCCGGAGCCCATCTCAGAGGCTTGACCC
                  V  L  A  D  S  N  F  V  R  S  P  S  Q  R  L  D  P>

↱ RRM2                                               1650
                CAGCAGGACGGTGTTTGTCGGTGCTCTGCATGGAATGCTAAATGCTGAGG
                   S  R  T  V  F  V  G  A  L  H  G  M  L  N  A  E

1700
                CCCTGGCAGCCATCTTGAACGACCTATTTGGTGGAGTGGTGTATGCCGGG
                 A  L  A  A  I  L  N  D  L  F  G  G  V  V  Y  A  G>

▽                  1750
                ATTGACACAGATAAGCACAAGTATCCCATTGGTTCTGGTCGTGTGACTTT
                 I  D  T  D  K  H  K  Y  P  I  G  S  G  R  V  T  F

1800
                CAATAACCAACGGAGTTACCTGAAAGCAGTCAGCGCTGCTTTTGTGGAGA
                  N  N  Q  R  S  Y  L  K  A  V  S  A  A  F  V  E>

▽                      ←↲        1850
                TCAAAACCACCAAGTTCACAAAGAAGGTTCAGATTGACCCCTACCTAGAA
                 I  K  T  T  K  F  T  K  K  V  Q  I  D  P  Y  L  E
```

Fig. 1E

```
                                                         Znf                                    1900
GATTCTCTGTGTCATATCTGCAGTTCTCAGCCTGGTCCTTTCTTCTGTCG
  D   S   L   C   H   I   C   S   S   Q   P   G   P   F   F   C   R>

1950
            ▽
AGATCAGGTCTGCTTCAAATACTTCTGCCGGAGCTGCTGGCACTGGCGGC
    D   Q   V   C   F   K   Y   F   C   R   S   C   W   H   W   R

2000
ACAGCATGGAGGGCCTGCGCCACCACAGCCCCCTGATGCGGAACCAGAAG
  H   S   M   E   G   L   R   H   H   S   P   L   M   R   N   Q   K>

2050
AACCGAGATTCCAGCTAGAGGAGCTGGCCTTGCCCAGTGGCCTGTGGCGC
  N   R   D   S   S   *>

2100
CCAAAGCTGGCAGGTCAGGCAAGCAGCCTGCACCACCCTGCCACTGGCGA

2150
CCAGGGAGCTGGCTTCCCAAGGACAAGGGAAAATTGTAGTCACCTTTGCA

2200
CTTGCTGAATCTGTCTTTGTTTCTGCACTAATTAATGCACATTGAGTTTT

2250
GTCAGGTTTTGTTTTCAGGGGGTGTACCAAGGGCAAGGACCCTCTGGCTT
```

Fig. 1F

```
                                                                2300
ACCCTCCAAGCGACTCTGTAGTTTTCCCAGATTTTAGTTCCTCATTTTGC

2350
AGATGAAAGCGGGGAAAAAAAAAAAAAAAAAATTCCTGAAGGTATTGA

2400
CACGGATGCCTACACCTAGGTTTATTTATTAAAAGCGCTTTTTTACATTC

2450
CTTGCAATACTGATGGTGATGATGCGCAGGTCTCATTGGTTTCATTCTTG

2500
CAGTTGCCATACAGTGCCTTTCCATTTATTTAACCCCCACCTGAACGGCA

2550
TAAACTGAGTGTTCAGCTGGTGTTTTTTACTGTAAACAATAAGGAGACTT

2600
TGCTCTTCATTTAAACCAAAATCATATTTCATATTTTACGCTCGAGGGTT

2650
TTTACCGGTTCCTTTTTACACTCCTTAAAACAGTTTTTAAGTCGTTTGGA

2700
AGAAAATATTTTTTCTTTCCTGGCAGCTTTTAACATTATAGCAAATTTGT

2750
GTCTGGGGGACTGCTGGTCACTGTTTCTCACAGTTGCAAATCAAGGCATT

TGCAACCAAAAAAAAAAAAAAAAAAAATG
```

Fig. 1G

```
                                                                       *50
GGCAGCGGGAAGCATCAGCAGCCTGATCACATGCTGGCCCAGTCTGTAAT

*            100
GCAGACGGGATAGGGGTGTGTGTGTGAGGGGAGGGGGCCTGTATGGCAAC

150
TGCTCTTGCCCCAGCGTCCCCAAAAGTGCAGAGGCAGCGGCTGCAGCATC

▼
CAGCCAGCTTGGATGTCTGGCCT
```

Fig. 1I

```
                          CPE     Hex
5'--------21nt-------  UUUUAU  AAUAAA  ----15nt----3;   wt UTR

5'--------21nt-------  UUUggU  AAUAAA  ----15nt----3'   mut UTR
```

HUMAN CYTOPLASMIC POLYADENYLATION ELEMENT BINDING PROTEIN AND USES THEREOF

CROSS-REFERENCE TO RELATED APPLICATION

This non-provisional application claims priority of provisional application U.S. Ser. No. 60/351,121, filed Jan. 23, 2002, now abandoned.

FEDERAL FUNDING LEGEND

This invention was produced in part using funds obtained through grant HD038081 from the National Institutes of Health. Consequently, the Federal government has certain rights in this invention.

BACKGROUND OF THE INVENTION

1. Field of the Invention

The present invention relates generally to the fields of molecular biology and gene cloning. More specifically, the present invention relates to the identification and characterization of the gene encoding human cytoplasmic polyadenylation element binding protein and uses thereof.

2. Description of the Related Art

During meiotic maturation of human oocytes gene transcription is repressed (Braude et al., 1988) and required proteins are translated from pre-existing, maternally derived mRNAs (Pal et al., 1994). In model systems (*Drosophila, Xenopus*, and the mouse), certain maternally derived mRNAs which encode key regulators of cell cycle progression and pattern formation are translationally silent in immature oocytes and become translationally activated following hormonal stimulation (Davidson, 1986; Wickens et al., 1996). This translational activation has been correlated with the cytoplasmic polyadenylation of the mRNAs, a process directed by two elements within the mRNA 3' untranslated region (UTR) (reviewed in Richter, 1999). The first element is the AAUAAA polyadenylation hexanucleotide and the second element is a uridine-rich sequence of general consensus UUUUUAU termed the cytoplasmic polyadenylation element (CPE). In addition to directing cytoplasmic polyadenylation and translational activation, these cytoplasmic polyadenylation element sequences have also been implicated in mediating translational repression in immature oocytes (de Moor and Richter, 1999; Barkoff et al., 2000; Tay et al., 2000) and during the early phases of hormonally stimulated oocyte maturation (Charlesworth et al., 2000). Cytoplasmic polyadenylation element-mediated mRNA translational control has also been suggested to occur in mammalian neuronal cells (Wu et al., 1998).

A cytoplasmic polyadenylation element binding protein, CPEB, has been cloned from a number of species (Hake and Richter, 1994; Gebauer and Richter, 1996; Bally-Cuif et al., 1998; Walker et al., 1999) and has been implicated in mediating both polyadenylation-dependent translational activation and cytoplasmic polyadenylation element-directed translational repression (Hake and Richter, 1994; Stebbins-Boaz et al., 1996; Stutz et al., 1998; Minshall et al., 1999; Stebbins-Boaz et al., 1999; Mendez et al., 2000). While it is not clear how the cytoplasmic polyadenylation element binding protein can exert these apparently opposite effects on mRNA translation, there is some evidence that the C-terminal domain is necessary for translational repression while the N-terminal domain may regulate translational activation. It has been reported that overexpression of an N-terminally truncated form of the *Xenopus* cytoplasmic polyadenylation element binding protein (lacking the first 139 amino acids) did not significantly affect translational repression but did block both cytoplasmic polyadenylation and translational induction (Mendez et al., 2000).

Given the key role of cytoplasmic polyadenylation in the control of mRNA translation in model organisms, it is of interest to determine if a similar process occurred in humans. However, human cytoplasmic polyadenylation element binding protein has not been identified. Thus, the prior art is deficient in identifying a human cytoplasmic polyadenylation element binding protein which is essential for the study of mRNA translation control in human. The present invention fulfills this long-standing need and desire in the art by cloning a human cytoplasmic polyadenylation element binding protein.

SUMMARY OF THE INVENTION

The present invention reports the cloning of a human cytoplasmic polyadenylation element binding protein (hCPEB) with sequence-specific RNA binding activity. The data disclosed herein demonstrate that alternative splicing generates human cytoplasmic polyadenylation element binding protein mRNAs that encode proteins with a conserved C-terminal RNA binding domain but with different N-terminal regulatory domains. The human cytoplasmic polyadenylation element binding protein mRNA is expressed in the brain and heart as well as in immature oocytes, consistent with the hypothesis that cytoplasmic polyadenylation may regulate the translation of human mRNAs in both oocytes and somatic cells.

In one embodiment of the present invention, there is provided an isolated DNA encoding human cytoplasmic polyadenylation element binding protein, expression vectors that contain the claimed DNA, as well as host cells that contains the expression vectors. The present invention also encompasses an isolated DNA which is complementary to the DNA disclosed herein.

The present invention further provides a recombinant human cytoplasmic polyadenylation element binding protein and polypeptides derived thereof. The human cytoplasmic polyadenylation element binding protein has the amino acid sequence of SEQ ID No. 3 or 4, and the polypeptide has at least 10 amino acid residues.

In another aspect of the present invention, there is provided a method of screening for compound that increases or decreases the RNA binding activity of human cytoplasmic polyadenylation element binding protein (hCPEB). The method involves the steps of (a) contacting human cytoplasmic polyadenylation element binding protein with a probe comprising cytoplasmic polyadenylation element (CPE) sequence in the presence of the compound; and (b) determining the cytoplasmic polyadenylation element sequence-specific binding activity of the human cytoplasmic polyadenylation element binding protein, wherein an increase in binding activity indicates the compound increases RNA binding activity of human cytoplasmic polyadenylation element binding protein, wherein a decrease in binding activity indicates the compound decreases RNA binding activity of human cytoplasmic polyadenylation element binding protein.

The present invention is also directed to a method of examining the reproductive potential of an oocyte, comprising the step of: determining the expression of human cytoplasmic polyadenylation element binding protein (hCPEB)

in the oocyte, wherein the presence of human cytoplasmic polyadenylation element binding protein expression indicates the oocyte has reproductive potential, wherein the lack of human cytoplasmic polyadenylation element binding protein expression indicates the oocyte lacks reproductive potential.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 1A–1J shows human cytoplasmic polyadenylation element binding protein sequence and alignment comparison. FIGS. 1A–1G shows $hCPEB_L$ cDNA sequence and predicted amino acid translation. Open arrowheads indicate the position of introns within the genomic human cytoplasmic polyadenylation element binding protein sequence and the closed arrowhead indicates the position of alternative splicing that yields the truncated $hCPEB_S$ variant. The predicted initiator methionine of $hCPEB_S$ is indicated. Methionine codons are underlined. An in-frame termination codon located 5' of the initiator methionine is indicated by an asterisk. The boundaries of the two RNA recognition motifs (RRM) and zinc finger domain (Znf) are bracketed. The two circled amino acids are putative Eg2 phosphorylation sites (Mendez et al., 2000). The unique BamHI site used to generate the ΔN-hCPEB protein is boxed.

FIG. 1H shows sequence comparison to other vertebrate cytoplasmic polyadenylation element binding proteins. RNA recognition motifs are indicated by hatched boxes, the zinc finger domain by a solid oval. Stippled boxes indicate the three blocks of conserved N-terminal protein homology between species (CPEB homology domains, CHD). CHD1 spans amino acids 22–53 of the $hCPEB_L$ protein; CHD2 spans amino acids 87–118; CHD3 spans amino acids 168–214. The percentages indicate the amino acid identity between the human and vertebrate cytoplasmic polyadenylation element binding proteins.

FIG. 1I shows the first non-coding exon of $hCPEB_S$. Primers specific to the putative $hCPEB_S$ were used to amplify a region that lay upstream of the coding sequence. An in-frame termination codon that was identified 162 bp 5' of the initiator methionine is indicated by an asterisk. Methionine codons in the 5' UTR are underlined. The closed arrowhead is the alternative splice site shown in FIG. 1A. An intron of greater than 25 kb separates this first $hCPEB_S$ exon from the upstream $hCPEB_L$ exon 2.

FIG. 1J shows human genomic DNA digested with the indicated enzymes and analyzed by Southern blotting for human cytoplasmic polyadenylation element binding protein gene complexity. A single 6 kb BamHI and a single 2.8 kb BamHI/BglII fragment cross-react with the human cytoplasmic polyadenylation element binding protein probe.

FIG. 2A shows human multiple tissue northern blots were probed with the human cytoplasmic polyadenylation element binding protein cDNA isolated from HeLa cells. PBL, peripheral blood leukocytes; sk. Muscle, skeletal muscle. An approximately 3300 nucleotide hCPEB mRNA is detected in ovary, brain and heart. The northern blot in the right panel has been exposed for twice the duration of the northern blot on the left to reveal human cytoplasmic polyadenylation element binding protein expression in the heart.

FIG. 2B shows RT-PCR analysis of human cytoplasmic polyadenylation element binding protein expression in immature human oocytes. Total RNA was prepared from two germinal vesicle intact immature human oocytes using STAT-60 (Tel-test) and RT-PCR performed in a single tube using 0.4 oocyte equivalents of total RNA and the primers (+) AGATG GGGGT AGGGT CTCGG A (SEQ ID NO. 5) and (−) GCAGC TTGTC GGTGC AGCCT G (SEQ ID NO. 6) to amplify a 180 bp product (oocyte RNA). Reverse transcription was performed at 60° C. followed by PCR amplification using 35 cycles of 94° C. for 30 s; 60° C. for 30 s; and 68° C. for 45 s. As specificity controls, PCR amplification was performed using 0.4 oocyte equivalents of total RNA but without prior reverse transcription (oocyte RNA, RT 2). No product was obtained indicating that the PCR product was not a result of amplification from any contaminating genomic DNA in the RNA preparation. Similarly, no product was amplified when water was used as template instead of RNA sample (water). As a positive control, RT-PCR was performed using HeLa RNA as template.

FIG. 4A is a schematic representation of the wild type (wt) and mutant (mut) Xenopus-Mos 3' UTR utilized as probes for gel shift analyses. The mut UTR probe encodes a two nucleotide substitution within the CPE sequence. The position of the polyadenylation hexanucleotide (Hex) AAUAAA is also shown.

FIG. 4B shows GST ΔN-hCPEB and the GST moiety alone were expressed in rabbit reticulocyte lysates and used for gel shift analyses with a radiolabeled wild type *Xenopus* Mos UTR probe. A solid arrowhead indicates specific complex formation between the radiolabeled probe and each GST-hCPEB fusion protein. The position of free probe is indicated. The GST ΔN-hCPEB/wt UTR complex was abolished using 50-fold excess unlabelled wt UTR probe but not with 50-fold excess unlabelled mut UTR probe. The GST ΔN-hCPEB/wt UTR complex could be supershifted with GST antiserum, but not with antiserum to B-Raf (open arrowhead). Several additional complexes were observed in the EMSA assay when incubated with unprogrammed reticulocyte lysate (UP) or GST moiety expressing lysate (open circles). However, these complexes were not supershifted by the GST antiserum and were competed by either unlabelled Mos wt UTR or mut UTR RNA, indicating that their formation was independent of the cytoplasmic polyadenylation element sequence or CPEB protein.

DETAILED DESCRIPTION OF THE INVENTION

The present invention reports the cloning of a human cytoplasmic polyadenylation element binding protein, hCPEB, which has CPE-specific RNA binding activity. The human cytoplasmic polyadenylation element binding protein is highly related to the cytoplasmic polyadenylation element binding proteins which have been previously cloned from frogs, mice, zebrafish and clams (Hake and Richter, 1994; Gebauer and Richter, 1996; Bally-Cuif et al., 1998; Walker et al., 1999). These proteins are all particularly conserved within the C-terminal RNA binding domain. Similar to the *Xenopus* and murine cytoplasmic polyadenylation element binding protein mRNAs, the hCPEB mRNA is expressed in immature oocytes (FIG. 2B) consistent with a presumptive role for the human cytoplasmic polyadenylation element binding protein in the translational regulation of mRNA in these cells.

The human cytoplasmic polyadenylation element binding protein mRNA is subject to alternative splicing and is predicted to yield products that encode cytoplasmic polyadenylation element binding proteins with different N-terminal extensions. An mRNA for a short form of hCPEB (hCPEB$_S$) which encodes an N-terminally truncated protein lacking the first conserved homology domain (CHD1) was identified. The hCPEB$_S$ mRNA is expressed in ovary, brain and heart.

Figure 1H:
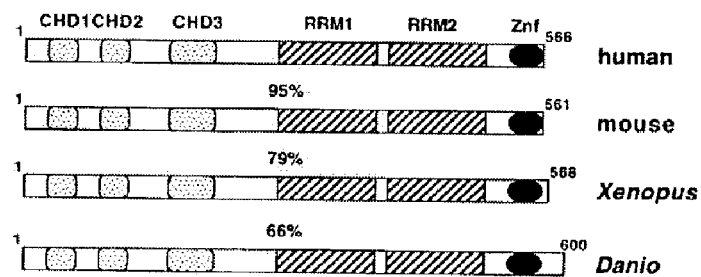
Figure 1J:
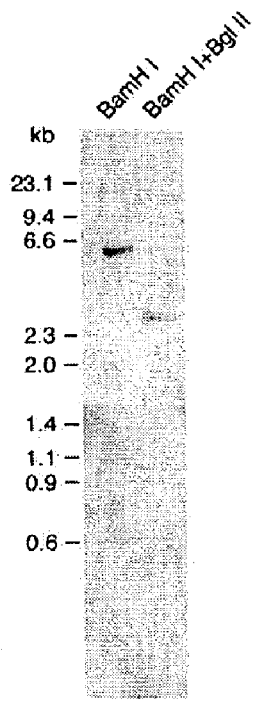

An alternatively spliced, long form of hCPEB (hCPEB$_L$) was also expressed in these tissues and encoded the N-terminal CHD1 region found in cytoplasmic polyadenylation element binding proteins from other vertebrate species (FIG. 1H). Since both human cytoplasmic polyadenylation element binding protein mRNA splice variants contain multiple AUG codons in their 5' UTRs and consequently may be subject to mRNA translational regulation, it will be particularly interesting to determine whether the presence of human cytoplasmic polyadenylation element binding protein mRNA directly correlates with human cytoplasmic polyadenylation element binding protein expression in human tissues.

In accordance with the present invention there may be employed conventional molecular biology, microbiology, and recombinant DNA techniques within the skill of the art. Such techniques are explained fully in the literature. See e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

The invention includes a substantially pure DNA encoding a human cytoplasmic polyadenylation element binding protein. Preferably, the DNA includes the coding sequence of the nucleotides of SEQ ID NOs: 1 or 2, or a degenerate variant of such sequences. The present invention encompasses DNA that have at least about 70% sequence identity to the coding sequence of the nucleotides listed in SEQ ID NOs: 1 or 2, preferably at least 75% (e.g. at least 80%); and most preferably at least 90%. "Substantially pure DNA" is DNA that is part of a milieu in which the DNA does not naturally occur. The DNA can be obtained by virtue of separation (partial or total purification) of some or all of the molecules of that milieu, or by virtue of alteration of sequences that flank the claimed DNA. The term therefore includes, for example, a recombinant DNA which is incorporated into a vector, an autonomously replicating plasmid or virus, the genomic DNA of a prokaryote or eukaryote; or which exists as a separate molecule (e.g., a cDNA, a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID NO: 1 which encodes an alternative splice variant of human cytoplasmic polyadenylation element binding protein.

The invention also includes DNA that hybridizes at high stringency to a probe containing at least 15 consecutive nucleotides of SEQ ID NOs: 1 or 2. The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID NOs: 1 or 2, or the complement thereof. Such a probe is useful for detecting expression of human cytoplasmic polyadenylation element binding protein in a cell by a method including the steps of (a) contacting mRNA obtained from the cell with the labeled hybridization probe; and (b) detecting hybridization of the probe with the mRNA.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

The present invention further comprises a vector comprising a DNA sequence which encodes a human cytoplasmic polyadenylation element binding protein and said vector comprises in operable linkage: a) an origin of replication; b) a promoter; and c) a DNA sequence coding for said protein. Preferably, the vector of the present invention contains a portion of the DNA sequence shown in SEQ ID Nos: 1 or 2.

A "vector" may be defined as a replicable nucleic acid construct, e.g., a plasmid or viral nucleic acid. Vectors may be used to amplify and/or express nucleic acid encoding human cytoplasmic polyadenylation element binding protein. An "expression vector" is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

As used herein, the term "host" is meant to include not only prokaryotes but also eukaryotes such as yeast, plant and animal cells. A recombinant DNA molecule or gene which encodes a human cytoplasmic polyadenylation element binding protein of the present invention can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

Further included in this invention are substantially pure human cytoplasmic polyadenylation element binding protein (hCPEB) which are encoded at least in part by portions of SEQ ID NOs: 1 or 2, or encoded by products of alternative mRNA splicing or alternative protein processing events, or in which a section of human cytoplasmic polyadenylation element binding protein sequence has been deleted.

By a "substantially pure protein" is meant a protein which has been separated from at least some of those components which naturally accompany it. Typically, the protein is substantially pure when it is at least 60% by weight free from the proteins and other naturally-occurring organic molecules with which it is naturally associated in vivo. Preferably, the purity of the preparation is at least 75%, more preferably at least 90%, and most preferably at least 99%, by weight. A substantially pure human cytoplasmic polyadenylation element binding protein may b e obtained, for example, by extraction from a natural source; by expression of a recombinant nucleic acid encoding a human cytoplasmic polyadenylation element binding protein polypeptide; or by chemically synthesizing the protein. Purity can be measured by any appropriate methods generally known to those of skill in the art. A protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the human cytoplasmic polyadenylation element binding protein (hCPEB, SEQ ID Nos: 3 or 4). As used herein, "fragment," as applied to a polypeptide, will ordinarily be at least 10 residues, more typically at least 20 residues, and preferably at least 30 (e.g., 50) residues in length, but less than the entire, intact sequence. Fragments of the human cytoplasmic polyadenylation element binding protein can be generated by methods known to those skilled in the art, e.g., by enzymatic digestion of naturally occurring or recombinant human cytoplasmic polyadenylation element binding protein, by recombinant DNA techniques using an expression vector that encodes a defined fragment of human cytoplasmic polyadenylation element binding protein, or by chemical synthesis. The ability of a candidate fragment to exhibit a characteristic of human cytoplasmic polyadenylation element binding protein (e.g., binding to cytoplasmic polyadenylation element sequence) can be assessed by methods described herein.

The fragment, or the intact human cytoplasmic polyadenylation element binding protein polypeptide, may b e covalently linked to another polypeptide, e.g. which acts as a label, a ligand or a means to increase antigenicity. Purified human cytoplasmic polyadenylation element binding protein or antigenic fragments thereof can be used to generate new antibodies or to test existing antibodies (e.g., as positive controls in a diagnostic assay) by employing standard protocols known to those skilled in the art. Any such antibody so generated, or a fragment thereof, may be linked to a toxin or to a detectable label generally known in the art, e.g. a radioactive label, non-radioactive isotopic label, fluorescent label, chemiluminescent label, paramagnetic label, enzyme label, or colorimetric label. Examples of suitable toxins include diphtheria toxin, *Pseudomonas* exotoxin A, ricin, and cholera toxin. Representative examples of suitable radioisotopic labels include $^{3}$H, $^{125}$I, $^{131}$I, $^{32}$P, $^{35}$S, $^{14}$C, etc.

The present invention provides a number of diagnostic advantages and uses. Given the potential key role of human cytoplasmic polyadenylation element binding protein (hCPEB) in the control of mRNA translation in cells such as oocytes and neurons, expression of human cytoplasmic polyadenylation element binding protein can be a diagnostic tool for assessing reproductive potential (e.g. infertility or low fertility) or brain functions such as learning, memory and cognitive functions. On the other hand, mutant forms of the human cytoplasmic polyadenylation element binding protein that have altered RNA binding activities can be used to modulate fertility and brain functions. Moreover, drugs can be targeted to block activated human cytoplasmic polyadenylation element binding protein functions in germ line and somatic tissue (e.g. brain) for the treatment of various disorders.

Antibodies (or antigen-binding fragments thereof) which bind to an epitope specific for human cytoplasmic polyadenylation element binding protein are useful in methods of detecting human cytoplasmic polyadenylation element binding protein in a biological sample. This method includes the steps of obtaining a biological sample (e.g. oocytes or brain cells), contacting the sample with a labeled antibody (e.g., radioactively tagged antibody) specific for human cytoplasmic polyadenylation element binding protein, and detecting the human cytoplasmic polyadenylation element binding protein using standard immunoassay techniques such as an ELISA. Likewise, a standard Northern blot assay can be used to ascertain the relative amounts of human cytoplasmic polyadenylation element binding protein mRNA in a cell or tissue in accordance with conventional Northern hybridization techniques known to those persons of ordinary skill in the art.

The present invention is directed to an isolated DNA encoding human cytoplasmic polyadenylation element binding protein, expression vectors that contain the claimed DNA, as well as host cells that contains the expression vectors. The claimed DNA includes DNA that has the sequence of SEQ ID No. 1 or 2, or DNA that encodes human cytoplasmic polyadenylation element binding protein but differs from SEQ ID No. 1 or 2 in codon sequence due to degeneracy of the genetic code. The host cell can be bacterial cells, mammalian cells, plant cells or insect cells. The present invention further encompasses an isolated DNA which is complementary to the DNA disclosed herein.

The present invention also provides a recombinant human cytoplasmic polyadenylation element binding protein and polypeptides derived thereof. The human cytoplasmic polyadenylation element binding protein has the amino acid sequence of SEQ ID No. 3 or 4, and the polypeptide has at least 10 amino acid residues.

In another aspect of the present invention, there is provided a method of screening for compound that increases or decreases the RNA binding activity of human cytoplasmic polyadenylation element binding protein (hCPEB). The method involves the steps of (a) contacting human cytoplasmic polyadenylation element binding protein with a probe comprising cytoplasmic polyadenylation element (CPE) sequence in the presence of said compound; and (b) determining the cytoplasmic polyadenylation element sequence-specific binding activity of, the human cytoplasmic polyadenylation element binding protein, wherein an increase in binding activity indicates said compound increases RNA binding activity of human cytoplasmic polyadenylation element binding protein, wherein a decrease in binding activity indicates said compound decreases RNA binding activity of human cytoplasmic polyadenylation element binding protein.

The present invention is also directed to a method of examining the reproductive potential of an oocyte, comprising the step of: determining the expression and/or activity of human cytoplasmic polyadenylation element binding protein (hCPEB) in said oocyte, wherein the presence of human cytoplasmic polyadenylation element binding protein expression or activity indicates said oocyte has reproductive potential, wherein the lack of human cytoplasmic polyadenylation element binding protein expression or activity indicates said oocyte lacks reproductive potential.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Plasmids Constructs and RNA Synthesis

Plasmid pGEM XeMos wt UTR was constructed as follows. The terminal 321 nucleotides of the Mos 3' UTR was cloned from immature oocytes by reverse transcription polymerase chain reaction (RT-PCR) to make pGEM Mos 321 UTR (Howard et al., 1999). A primer with a 5' BamHI site (+) GCGGG ATCCA TTCCA TATGT GAATA TATAG (SEQ ID NO. 11) was designed to amplify the last 48 nucleotides of the Mos 3' UTR from pGEM Mos 321 UTR. The reverse primer was the T7 promoter primer TAATA CGACT CACTA TAGGG (SEQ ID NO. 12). The PCR product was cut with BamHI/HindIII and inserted into BamHI/HindIII digested pGEM4Z. The size of the probe after in vitro transcription with SP6 RNA polymerase was 82 nt (48 nt that correspond to Mos UTR, and 34 nt that derive from the pGEM polylinker). The integrity of the probe was confirmed by DNA sequencing.

Plasmid pGEM XeMos mut UTR was constructed as follows. The terminal 321 nucleotides of the Mos 3' UTR was cloned from immature oocytes by RT-PCR. PCR primers were designed to include 5' BamHI (+) CGCGG ATCCC CCGGG CACTA GTAGC CAGGA GTTCA T (SEQ ID NO. 13) and 3' XbaI (−) CGTCT AGACA AATCA ATTTC TTTAT TACCA AACTA TATAT TC (SEQ ID NO. 14) restriction sites. The 3' (−) primer substituted a mutant CPE sequence, TTTggT, for the wild type TTTTAT. The resulting PCR product was cloned into BamHI/XbaI digested pGEM4Z (Promega) and designated pGEM Mos M3. The integrity of the Mos UTR was confirmed by DNA sequencing. The mutant EMSA probe was made from the pGEM Mos M3 template using the same strategy and primers as for the wild type probe above. The integrity of the probe was confirmed by DNA sequencing.

For in vitro transcription to generate radiolabeled RNA gel shift probes, pGEM XeMos wt UTR and pGEM XeMos mut UTR were linearized with XbaI, transcribed with the SP6 RNA polymerase (Melton et al., 1984) and 50 mM UTP, 0.5 mM ATP, 0.5 mM CTP, 0.5 mM GTP and 50 mCi of [$\alpha$-$^{32}$P]UTP (400 Ci/mmol, Amersham).

EXAMPLE 2

Northern and Southern Blot Analyses

Human multiple tissue northern blots (2 µg polyA+RNA per lane) (Clontech) were probed with a 1326 bp BamHI/

XcmI fragment of clone H12139 radioactively labeled using the random primer labeling kit (Pharmacia) and [α-$^{32}$P] dCTP (Amersham). Following overnight hybridization at 55° C., the membranes were washed twice in 1×SSC (0.15 M NaCl, 0.015 M sodium citrate)-0.5% SDS for 10 min at 55° C. and twice in 0.1×SSC-0.1% SDS for 30 min at 55° C. and analyzed by autoradiography. For Southern analysis, 10 ug of human genomic DNA was digested with the indicated enzymes, transferred to nitrocellulose and probed with a multimerized probe corresponding to nucleotides 543–765 of hCPEB$_L$. Filters were washed twice with 2×SSC, 0.1% SDS for 10 min at room temperature and twice 0.1×SSC, 0.1% SDS for 30 min at 65° C. and analyzed by autoradiography.

EXAMPLE 3

Human Oocyte Harvest and RT-PCR Analysis

Germinal vesicle-intact human oocytes were collected from consenting patients following a protocol approved by the Institutional Review Board at the University of Michigan. Oocyte-cumulus masses were collected into HEPES-buffered human tubule fluid media containing 3% (vol/vol) human serum albumin (HTF-H3; Irvine Scientific, Santa Ana, Calif.) by transvaginal follicular aspiration after controlled ovarian stimulation (Pool and Martin, 1994). Cumulus and corona radiata cells were removed by brief exposure to HTF-H3 containing 80 IU hyaluronidase (Sigma, St. Louis, Mo.) followed by mechanical pipetting through flame-pulled Pasteur pipettes. Complete absence of non-gamete cells and presence of germinal vesicle were confirmed using an inverted microscope with Hoffman optics at 400×. Germinal vesicle-intact oocytes were pooled, frozen in liquid nitrogen and stored at −80° C. until analyses were performed. RT-PCR was performed as described below.

EXAMPLE 4

RNA Electrophoretic Mobility Shift Assays (EMSA)

An N-terminally truncated form of human cytoplasmic polyadenylation element binding protein that was common to both splice variants, (GST ΔN-hCPEB), was generated for analysis of hCPEB sequence-specific RNA binding activity. Clone H12139, in Lafmid BA vector, was digested with NarI (located 27 bp downstream of the termination codon in the hCPEB 3' UTR), blunted with Klenow, and digested with BamH1 to yield a 1288 bp fragment, ΔN-hCPEB. This was then ligated in-frame to the N-terminal GST moiety of the pXen1 expression vector (MacNicol et al., 1997) to generate pXen ΔN-hCPEB. Protein for EMSA experiments was prepared by coupled transcription/translation using SP6 RNA polymerase (Promega), non-radioactively labeled methionine and a rabbit reticulocyte lysate system (TNT Coupled System, Promega) according to the manufacturer's protocol. GST ΔN-human cytoplasmic polyadenylation element binding protein levels were normalized relative to the level of the GST moiety expressed alone by anti-GST Western blotting and densitometry. The GST moiety was expressed from the pXen1 vector lacking any insert. EMSA binding reactions, competition experiments and supershift assays were performed as previously described (Charlesworth et al., 2000).

EXAMPLE 5

Identification of the Gene Encoding the Human Cytoplasmic Polyadenylation Element Binding Protein (hCPEB)

Human EST's with homology to the *Xenopus* CPEB cDNA were identified in GenBank using BLAST (Altschul et al., 1997). Three cDNA clones H12139, N54198 and AA323191 were sequenced completely and found to encode partially overlapping sequence. These sequences contained a 491 amino acid open reading frame predicted to encode a protein of approximately 55 kD. 5' RACE was used to obtain extended human CPEB sequence from Marathon-Ready human ovary cDNA (Clontech) using an hCPEB-specific reverse primer (5' (−) GGGGA TCCAG AGGCA GGAAG CTCAA, SEQ ID NO. 15). Multiple independent cDNA clones representing two alternative 5' sequences were obtained and designated hCPEB short (hCPEB$_S$) and hCPEB long (hCPEB$_L$). A subsequent BLAST search of the human genome sequence (NCBI) identified three overlapping contigs that matched the hCPEB$_L$ and hCPEB$_S$ cDNA sequences (GenBank AC010724; AC011140 and AC068126).

Analysis of the human genomic sequence revealed the presence of 14 exons spanning greater than 54 kb. The genomic sequence indentified the first exon sequence of hCPEB$_L$ included the first five amino acids with a predicted initiator methionine and was separated from the exon encoding amino acids six through 63 by a 771 bp intron. Characterization of intron/exon boundaries revealed that the hCPEB$_L$ and the hCPEB$_S$ sequences arise as a consequence of alternative splicing (see FIG. 1A-1J). The sequences of human cytoplasmic polyadenylation element binding protein long (AF329402) and human cytoplasmic polyadenylation element binding protein short (AF329403) have been submitted to GenBank.

An alignment of the human cytoplasmic polyadenylation element binding protein genomic sequence with the known cDNA sequences of murine, *Xenopus* and zebrafish (Hake and Richter, 1994; Gebauer and Richter, 1996; Bally-Cuif et al., 1998) allowed us to delimit the N-terminus of hCPEB$_L$. While the N-terminal domain of CPEB is less well conserved between species than the C-terminal domain, three blocks of homology (CPEB homology domain, CHD) are apparent (FIG. 1H).

A short form of CPEB has not been previously described. To establish that hCPEB$_S$ represented a naturally occurring mRNA, a cDNA encoding this protein was amplified via RT-PCR from human ovary RNA and HeLa cells. DNA sequencing (FIG. 1I) confirmed the presence of an in-frame stop codon, 162 bp upstream of the putative initiator methionine. When compared to the murine, *Xenopus* and zebrafish cDNA sequences, the predicted hCPEB$_S$ protein lacked 75, 76 and 74 N-terminal amino acids respectively, suggesting that this is a truncated form of the cytoplasmic polyadenylation element binding protein. The predicted hCPEB$_S$ protein lacks CHD1 but contains CHD2 which is serine and leucine rich. The hCPEB$_S$ also contains CHD3 which is serine, proline and glycine rich and encodes sites of proposed regulatory phosphorylation (Mendez et al., 2000) and a region resembling a PEST degradation sequence (Rechsteiner and Rogers, 1996).

Alignment of the hCPEB$_S$ and hCPEB$_L$ cDNA with the human cytoplasmic polyadenylation element binding protein genomic sequence revealed that alternative splicing generates the hCPEB$_L$ and hCPEB$_S$ mRNA species. Interestingly, the 5' UTR of both hCPEB mRNA splice variants encode multiple upstream AUG codons (FIG. 1A-1G), 1I, suggesting that the translation of the hCPEB$_L$ and hCPEB$_S$ mRNAs may be tightly regulated (reviewed in Gray and Wickens, 1998). The 5' UTR of hCPEB$_L$ contains five in-frame AUG codons (FIG. 1A-1G, doubly underlined) between the upstream in-frame STOP codon and the predicted initiator methionine of hCPEB$_L$, raising the possibility that alternative initiator methionine AUG utilization may produce hCPEB$_L$ protein variants with different N-terminal amino acid sequence. The other six AUG codons initiate short open reading frames that terminate within the hCPEB$_L$ 5' UTR prior to the predicted initiator methionine. All upstream AUG codons in the hCPEB$_S$ 5' UTR are in alternative reading frames. No upstream AUG codons are found in the 5' UTRs off the frog, zebrafish or mouse CPEB mRNAs, although the reported mouse 5' UTR is likely incomplete (Gebauer and Richter, 1996). While the zebrafish CPEB mRNA lacks upstream AUGs, it may be subject to translational regulation since the 3' UTR contains a cytoplasmic polyadenylation element sequence (Bally-Cuif et al., 1998).

To determine if human cytoplasmic polyadenylation element binding protein was part of a multi-gene family, a region common to both human cytoplasmic polyadenylation element binding protein mRNA splice variants was used to probe restriction enzyme digested human genomic DNA. Single cross-reacting fragments were identified (FIG. 1J), suggesting that human cytoplasmic polyadenylation element binding protein may be encoded by a single gene. Consistent with this interpretation, no additional human genome sequence contigs that had significant homology to human cytoplasmic polyadenylation element binding protein were identified in the NCBI database.

A comparison of the predicted amino acid sequence of the hCPEBL protein revealed an overall 95% identity to mouse cytoplasmic polyadenylation element binding protein (FIG. 1H), with particularly high homology between the RNA recognition motifs (RRMs) and the C-terminal zinc finger motif (Znf). Similar to the *Xenopus* protein, the hCPEB$_L$ protein ends with RDSS, a sequence deleted in the murine cytoplasmic polyadenylation element binding protein (Gebauer and Richter, 1996). Both hCPEB$_L$ and hCPEB$_S$ isoforms contain two conserved putative Eg2 phosphorylation sites (Mendez et al., 2000) (FIG. 1A-1G, circled), although the first Eg2 motif encodes threonine instead of the serine residue found in *Xenopus* CPEB.

EXAMPLE 6

Expression of the Human CPEB mRNA in Human Tissues

Figure 2A:
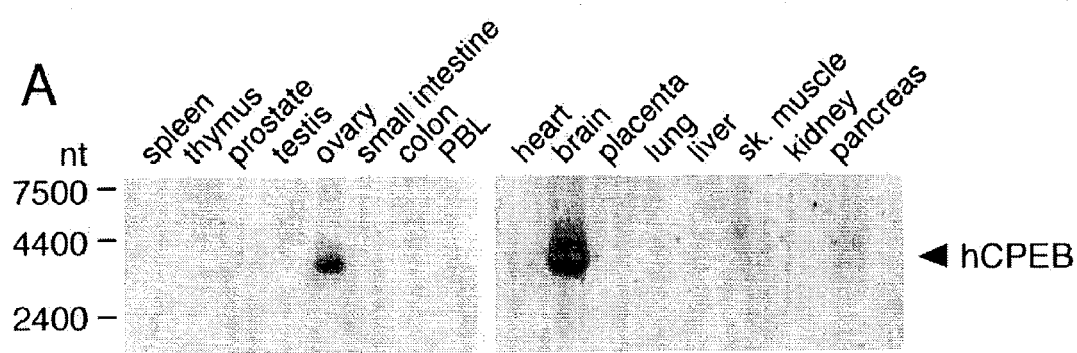
FIGS. 2A–2B show human cytoplasmic polyadenylation element binding protein expression patterns in adult human tissue.

To determine the expression pattern of the human cytoplasmic polyadenylation element binding protein homologue, multiple tissue northern blots were probed with radiolabeled hCPEB cDNA corresponding to the C-terminal half of the coding region which is identical in both hCPEB$_L$ and hCPEB$_S$ mRNAs. High levels of hCPEB mRNA were detected in adult ovary and brain with lower levels detected in the heart (FIG. 2A). The difference in size between the hCPEB cDNA sequences and the mRNA species detected in these tissues may be due to extended 5' UTR sequence. Cytoplasmic polyadenylation element binding protein cross-reactive bands were also detected in pancreas and skeletal muscle but are larger than the species detected in ovary, heart and brain. These larger bands may derive from the alternative splicing of additional, as yet uncharacterized, human cytoplasmic polyadenylation element binding protein exons or may derive from an as yet unidentified human cytoplasmic polyadenylation element binding protein-related gene.

Figure 2B:
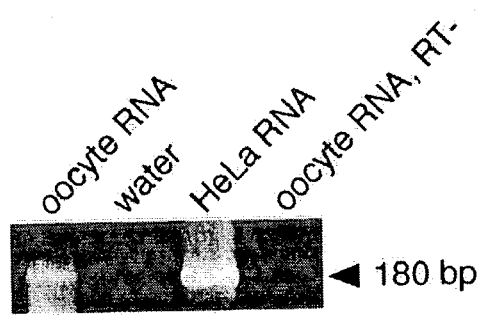

It has been previously demonstrated that the *Xenopus* and murine cytoplasmic polyadenylation element binding protein mRNAs are expressed in immature oocytes (Hake and Richter, 1994; Gebauer and Richter, 1996). To determine if human cytoplasmic polyadenylation element binding protein was expressed in immature human oocytes, RT-PCR analysis was performed using a PCR primer combination that does not discriminate between the long and short forms of human cytoplasmic polyadenylation element binding protein. As can be seen in FIG. 2B, hCPEB mRNA is indeed expressed in immature human oocytes.

Figure 3:
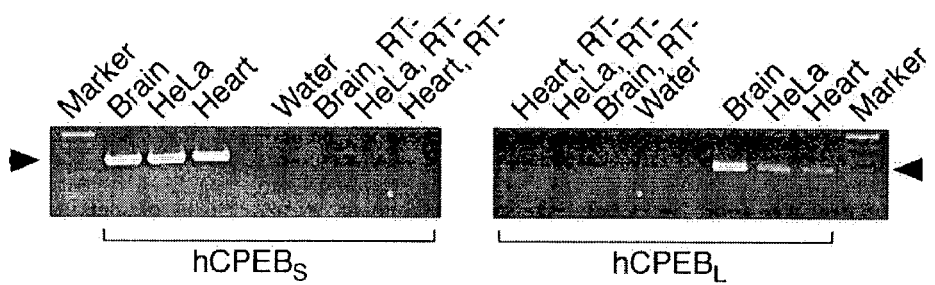
FIG. 3 shows alternatively spliced forms of human cytoplasmic polyadenylation element binding protein expressed in brain and heart. For analysis of differential expression of $hCPEB_L$ and $hCPEB_S$ mRNAs, 200 ng of human brain, heart or HeLa cell total RNA were reverse transcribed using either $hCPEB_L$ (−) GCATC CTGCT TGTAA CTGTT (SEQ ID NO. 7) or $hCPEB_S$ (−) GGACT GCAGG CCAAG GCA (SEQ ID NO. 8). Subsequent PCR amplification of the long form of human cytoplasmic polyadenylation element binding protein was obtained using both the $hCPEB_L$ (−) primer and $hCPEB_L$ (+) GGAAG AAGAA GCAGG AAGGA T (SEQ ID NO. 9) to amplify a 215 bp product (right panel). For PCR amplification of the short form of human cytoplasmic polyadenylation element binding protein, both the $hCPEB_S$ (−) primer and $hCPEB_S$ (+) GCGGA ATTCC AGCGG GAAGC ATCAG CAG (SEQ ID NO. 10) were used to amplify a 283 bp product (left panel). PCR parameters were the same for both $hCPEB_L$ and $hCPEB_S$ primer pairs: 35 cycles of 94° C. for 30 seconds; 40° C. for 30 seconds; and 72° C. for 48 seconds. As controls for specificity, PCR amplification was performed without prior reverse transcription (RT−) and in all cases no PCR product was obtained. Similarly, no product was amplified when water was used as template instead of RNA sample (water). All PCR products were sequenced to verify the integrity of the amplified region of human cytoplasmic polyadenylation element binding protein.

When PCR primers specific for the hCPEB$_L$ and hCPEB$_S$ isoforms were utilized, it was found that both the hCPEB$_L$ and hCPEB$_S$ splice variants are expressed in human brain and heart tissue as well as in the HeLa cell line (FIG. 3). The RT-PCR data suggest that the hCPEB$_L$ mRNA may be preferentially expressed in the brain, whereas the hCPEB$_S$ transcript does not show any appreciable difference in levels between brain and heart tissue.

The expression of mRNA encoding human cytoplasmic polyadenylation element binding protein in human brain is interesting in light of a recent study which suggests that cytoplasmic polyadenylation element-regulated mRNA translational control may function in the brain. Specifically, cytoplasmic polyadenylation element sequences and the cytoplasmic polyadenylation element binding protein have been implicated in the control of CaMKIIα mRNA cytoplasmic polyadenylation and translation during long term potentiation in the rat hippocampus (Wu et al., 1998). No human mRNAs have yet been identified which contain functional cytoplasmic polyadenylation element sequences. However, a survey of vertebrate 3' UTRs suggest that potential cytoplasmic polyadenylation element sequences exist in a variety of human mRNAs (Pesole et al., 2000), including some mRNAs implicated in regulating oocyte maturation (e.g. Raf-1, Wee1) and neuronal function (e.g. FGF receptor 1, PTPζ).

EXAMPLE 7

Human CPEB is a Sequence Specific RNA Binding Protein

To determine if human cytoplasmic polyadenylation element binding protein possessed cytoplasmic polyadenylation element-sequence specific RNA binding activity, human cytoplasmic polyadenylation element binding protein was incubated with a radiolabeled RNA probe corresponding to the terminal 48 nucleotides of the wild-type *Xenopus* Mos 3' UTR (wt UTR, FIG. 4A) and binding was determined in an electrophoretic mobility shift assay (EMSA). The *Xenopus* Mos 3' UTR was used to characterize hCPEB RNA binding properties since it has previously been shown to interact with the heterologous murine cytoplasmic polyadenylation element binding protein as well as the *Xenopus* CPEB (Gebauer and Richter, 1996; Stebbins-Boaz et al., 1996).

For these experiments, an N-terminal deletion of hCPEB (ΔN hCPEB) which contains all the characterized RNA interaction domains and possesses sequence common to both the hCPEB$_L$ and hCPEB$_S$ splice variants was utilized. The ΔN human cytoplasmic polyadenylation element binding protein protein was expressed as an in-frame fusion to an N-terminal GST epitope tag following in vitro transcription and translation in rabbit reticulocyte lysates. The GST moiety expressed alone or unprogrammed lysate (UP) was also utilized to enable a distinction between non-specific and specific interactions with the Mos 3' UTR probe.

Figures 4A, 4B:
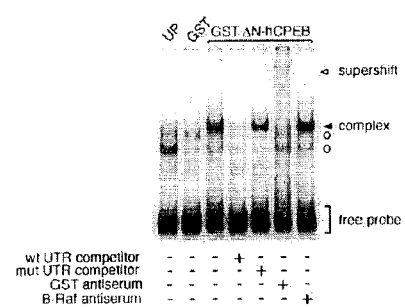
FIGS. 4A–4B show human cytoplasmic polyadenylation element binding protein is a sequence-specific RNA binding protein.

As shown in FIG. 4B, the ΔN hCPEB protein formed a specific complex with the Mos UTR probe. Specific complexes did not form with the GST moiety alone or unprogrammed lysate (UP). Complex formation was dependent upon the cytoplasmic polyadenylation element sequence within the Mos UTR probe because addition of a 50-fold excess of unlabelled 3' UTR effectively competed GST ΔN hCPEB interaction with radiolabeled Mos UTR. In contrast, a 50-fold excess of unlabelled mutant 3' UTR encoding a 2 nucleotide substitution within the CPE (FIG. 4A, mut UTR) did not compete GST ΔN hCPEB/Mos UTR binding (FIG. 4B). The presence of human cytoplasmic polyadenylation element binding protein in the specific Mos UTR complexes was verified by a supershift analysis. Antiserum against the N-terminal GST tag effectively supershifted the GST ΔN hCPEB/Mos UTR complex (FIG. 4B). Antiserum against an unrelated protein, B-Raf, did not elicit a supershift of the hCPEB/Mos UTR complex (FIG. 4B).

The mechanism(s) by which the cytoplasmic polyadenylation element binding protein regulates mRNA translation has not been fully elucidated. The ability of cytoplasmic polyadenylation element binding protein to interact with cytoplasmic polyadenylation element-containing RNA target sequences has been shown to require the evolutionarily conserved C-terminal RNA recognition motifs and zinc finger domain (Hake et al., 1998). The cytoplasmic polyadenylation element binding protein is associated with cytoplasmic polyadenylation element-containing mRNAs in both immature and mature *Xenopus* oocytes (Hake and Richter, 1994; Stebbins-Boaz et al., 1996). The cytoplasmic polyadenylation element binding protein N-terminal domain may function to promote translational activation in maturing oocytes. This domain contains sites of maturation-dependent phosphorylation (Mendez et al., 2000) and a recent study has demonstrated that mutation of two N-terminal Eg2 phosphorylation sites or deletion of the first 139 amino acids of the N-terminal domain generates an inhibitory, dominant negative form of the *Xenopus* cytoplasmic polyadenylation element binding protein. These dominant negative cytoplasmic polyadenylation element binding proteins prevent translational activation and cytoplasmic polyadenylation but maintain cytoplasmic polyadenylation element-directed translational repression in maturing oocytes (Mendez et al., 2000). The predicted hCPEBS protein contains both the C-terminal RNA binding domain and the N-terminal sites of Eg2 regulatory phosphorylation. The absence of the CHD1 in hCPEB$_S$ domain may confer altered regulatory properties to the hCPEB$_S$ protein or alter the subcellular localization of the hCPEB$_S$ protein (Wu et al., 1998). Further characterization of the properties of the alternatively spliced forms of the human cytoplasmic polyadenylation element binding protein protein may provide insight into the role of the N-terminal domain of the cytoplasmic polyadenylation element binding protein in mediating mRNA translational control.

The following references were cited herein:

Altschul et al., (1997). Gapped BLAST and PSI-BLAST: a new generation of protein database search programs. Nucleic Acids Res. 25:3389–3402.

Bally-Cuif et al., (1998). Characterization of the zebrafish Orb/CPEB-related RNA binding protein and localization of maternal components in the zebrafish oocyte. Mech. Dev. 77:31–47.

Barkoff et al., (2000). Translational control of cyclin B1 mRNA during meiotic maturation: coordinated repression and cytoplasmic polyadenylation. Dev. Biol. 220:97–109.

Braude et al., (1988). Human gene expression first occurs between the four- and eight-cell stages of preimplantation development. Nature 332:459–461.

Charlesworth et al., (2000). The temporal control of Wee1 mRNA translation during oocyte maturation is regulated by cytoplasmic polyadenylation elements within the 3' untranslated region. Dev. Biol., in press.

Davidson (1986). Gene activity in early development, 3rd Edition. Academic Press, London.

de Moor and Richter, (1999). Cytoplasmic polyadenylation elements mediate masking and unmasking of cyclin B1 mRNA. EMBO J. 18:2294–2303.

Gebauer and Richter, (1996). Mouse cytoplasmic polyadenylation element binding protein: an evolutionarily conserved protein that interacts with the cytoplasmic polyadenylation elements of c-mos mRNA. Proc. Natl. Acad. Sci. 93:14602–14607.

Gray and Wickens, (1998). Control of translation initiation in animals. Annu. Rev. Cell Dev. Biol. 14:399–458.

Hake and Richter, (1994). CPEB is a specificity factor that mediates cytoplasmic polyadenylation during *Xenopus* oocyte maturation. Cell 79:617–627.

Hake et al., (1998). Specificity of RNA binding by CPEB: requirement for RNA recognition motifs and a novel zinc finger. Mol. Cell. Biol. 18:685–693.

Howard et al., (1999). The mitogen-activated protein kinase signaling pathway stimulates mos mRNA cytoplasmic polyadenylation during *Xenopus* oocyte maturation. Mol. Cell. Biol. 19:1990–1999.

MacNicol et al., (1997). pXen, a utility vector for the expression and purification of GST-fusion proteins in *Xenopus* oocytes and embryos. Gene 196:25–29.

Melton et al., (1984). Efficient in vitro synthesis of biologically active RNA and RNA hybridization probes from plasmids containing a bacteriophage SP6 promoter. Nucleic Acids Res. 12:7035–7056.

Mendez et al., (2000). Phosphorylation of CPE binding factor by Eg2 regulates translation of c-mos mRNA. Nature 404:302–307.

Minshall et al., (1999). Dual roles of p82, the clam CPEB homolog, in cytoplasmic polyadenylation and translational masking. RNA 5:27–38.

Pal et al., (1994). Expression and potential function of the c-mos proto-oncogene in human eggs. Fertil. Steril. 61:496–503.

Pesole et al., (2000). UTRdb and UTRsite: specialized databases of sequences and functional elements of 5' and 3' untranslated regions of eukaryotic mRNAs. Nucleic Acids Res. 28:193–196.

Pool and Martin, (1994). High continuing pregnancy rates after in vitro fertilization-embryo transfer using medium supplemented with a plasma protein fraction containing alpha- and beta-globulins. Fertil. Steril. 61:714–719.

Rechsteiner and Rogers, (1996). PEST sequences and regulation by proteolysis. Trends Biochem. Sci. 21:267–271.

Richter, (1999). Cytoplasmic polyadenylation in development and beyond. Microbiol. Mol. Biol. Rev. 63:446–456.

Stebbins-Boaz et al., (1996). CPEB controls the cytoplasmic polyadenylation of cyclin, Cdk2 and c-mos mRNAs and is necessary for oocyte maturation in *Xenopus*. EMBO J. 15:2582–2592.

Stebbins-Boaz et al., (1999). Maskin is a CPEB-associated factor that transiently interacts with eIF-4E. Mol. Cell. 4:1017–1027.

Stutz et al., (1998). Masking, unmasking, and regulated polyadenylation cooperate in the translational control of a dormant mRNA in mouse oocytes. Genes Dev. 12:2535–2548.

Tay et al., (2000). The control of cyclin B1 mRNA translation during mouse oocyte maturation. Dev. Biol. 221: 11–9.

Walker et al., (1999). The clam 3' UTR masking element-binding protein p82 is a member of the CPEB family. RNA 5:14–26.

Wickens et al., (1996). Translational Control of Developmental Decisions. In: Hershey, et al. (Eds.), Translational Control. Cold Spring Harbor Laboratory Press, Plainview, N.Y., pp. 411–450.

Wu et al., (1998). CPEB-mediated cytoplasmic polyadenylation and the regulation of experience-dependent translation of alpha-CaMKII mRNA at synapses. Neuron 21:1129–1139.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A recombinant human cytoplasmic polyadenylation element binding protein, wherein said protein has the amino acid sequence of SEQ ID NO: 3 or 4.

2. A method of screening for a compound that increases or decreases the RNA binding activity of a human cytoplasmic polyadenylation element binding protein comprising SEQ ID NO: 3 or 4, comprising the steps of:
   (a) contacting said human cytoplasmic polyadenylation element binding protein with an RNA probe comprising the cytoplasmic polyadenylation element sequence in the presence of said compound, and
   (b) determining the cytoplasmic polyadenylation element sequence-specific binding activity of said polyadenylation element binding protein, wherein an increase in said binding activity indicates that said compound increases the RNA binding activity of the human cytoplasmic polyadenylation element binding protein, and wherein a decrease in said binding activity indicates that said compound decreases the RNA binding activity of the human cytoplasmic polyadenylation element binding protein.

* * * * *

```
                        SEQUENCE LISTING

<160> NUMBER OF SEQ ID NOS: 16

<210> SEQ ID NO 1
<211> LENGTH: 2779
<212> TYPE: DNA
<213> ORGANISM: Homo sapiens
<220> FEATURE:
<221> NAME/KEY: prim_transript
<223> OTHER INFORMATION: cDNA sequence of the long form of cytoplasmic
      polyadenylation element binding protein

<400> SEQUENCE: 1
taatgtcaat atgttttctg gcattgctac ttcaacatcg tcttccatgt            50
ctggcactgg tttggagcac tcatctctat cagattgtct tctgctaatt           100
cctctggtat gttaactctt ggatttctcc aaggtccatg tcttggaaat           150
cttcactccc aacctttttt tgtcatatct acagtttctt tcatgatttc           200
ctgtattggc tctgtggtaa atctgtgaag tcatgtacaa catctggaaa           250 cagtttttt aagcaggaat ttattatttt gggcatgatg gctttcatgg            300
atttttctgt aacaatgatg gcattgtcac tggaagaaga agcaggaagg           350
ataaaagatt gctgggacaa ccaggaagca cctgctctct ccacgtgtag           400
taatgccaat atctttcgaa ggataaatgc catattggat aattctctgg           450
atttcagtag agtctgcact acacctataa accgaggaat tcatgatcat           500
ttgccagact ccaggactc tgaagaaaca gttacaagca ggatgctttt            550
cccaacctct gcgcaagaat cttcccgtgg cctcccagat gcaaatgact           600
tgtgccttgg cctgcagtcc ctcagtctga caggctggga ccgaccctgg           650
agcacccagg actcagattc ctcagcccag agcagcacac actcggtact           700
gagcatgctc cataacccac tgggaaatgt cctaggaaaa ccccccttga           750
gcttcctgcc tctggatccc cttgggtctg acttggtgga caagtttcca           800
gcaccctcag ttagaggatc acgcctggac acccggccca tcctggactc           850
tcgatctagc agcccctctg actcagacac cagtggcttc agctctggat           900
cagatcatct ctcagatttg atttcaagcc ttcgcatttc tccacctctg           950
cccttcctgt ctctgtcagg gggtggtccc agagacccctt taaagatggg          1000 ggtagggtct cggatggacc aagagcaagc tgctcttgct gcagtcactc           1050
cctccccaac cagtgcttca aagagatggc caggagcttc tgtgtggcca           1100
tcctgggacc tcctcgaagc tcccaaagac cccttcagca tagagagaga           1150
```

| | |
|---|---|
| ggccaggctg caccgacaag ctgcagctgt gaatgaagcc acctgtacct | 1200 |
| ggagtggcca gcttcctccc cggaactata agaaccccat ctactcttgc | 1250 |
| aaggtgtttc taggaggtgt tccttgggat attacagaag ctggattagt | 1300 |
| taacaccttc cgtgtttttg gctctttgag tgtggagtgg cctggtaagg | 1350 |
| atggcaagca tccccggtgt cctcccaaag gtaatatgcc taaagggtat | 1400 |
| gtgtatctgg tcttcgaact agagaagtct gtccgatcct tgcttcaggc | 1450 |
| ttgctctcat gacccgctga gcccagatgg cctgagtgaa tattatttca | 1500 |
| agatgtccag ccgaaggatg cgctgcaagg aggtgcaggt gatcccctgg | 1550 |
| gtattagccg acagtaactt tgtccggagc ccatctcaga ggcttgaccc | 1600 |
| cagcaggacg gtgtttgtcg gtgctctgca tggaatgcta aatgctgagg | 1650 |
| ccctggcagc catcttgaac gacctatttg gtggagtggt gtatgccggg | 1700 |
| attgacacag ataagcacaa gtatcccatt ggttctggtc gtgtgacttt | 1750 |
| caataaccaa cggagttacc tgaaagcagt cagcgctgct tttgtggaga | 1800 |
| tcaaaaccac caagttcaca aagaaggttc agattgaccc ctacctagaa | 1850 |
| gattctctgt gtcatatctg cagttctcag cctggtcctt tcttctgtcg | 1900 |
| agatcaggtc tgcttcaaat acttctgccg gagctgctgg cactggcggc | 1950 |
| acagcatgga gggcctgcgc caccacagcc ccctgatgcg gaaccagaag | 2000 |
| aaccgagatt ccagctagag gagctggcct tgcccagtgg cctgtggcgc | 2050 |
| ccaaagctgg caggtcaggc aagcagcctg caccaccctg ccactggcga | 2100 |
| ccagggagct ggcttcccaa ggacaaggga aaattgtagt caccttttgca | 2150 |
| cttgctgaat ctgtctttgt ttctgcacta attaatgcac attgagttttt | 2200 |
| gtcaggtttt gttttcaggg ggtgtaccaa gggcaaggac cctctggctt | 2250 |
| accctccaag cgactctgta gttttcccag attttagttc ctcattttgc | 2300 |
| agatgaaaag cggggaaaaa aaaaaaaaaa aaaattcctg aaggtattga | 2350 |
| cacggatgcc tacacctagg tttatttatt aaaagcgctt ttttacattc | 2400 |
| cttgcaatac tgatggtgat gatgcgcagg tctcattggt ttcattcttg | 2450 |
| cagttgccat acagtgcctt tccatttatt taaccccccac ctgaacggca | 2500 |
| taaactgagt gttcagctgg tgttttttac tgtaaacaat aaggagactt | 2550 |
| tgctcttcat ttaaaccaaa atcatatttc atattttacg ctcgagggtt | 2600 |
| tttaccggtt cctttttaca ctccttaaaa cagtttttaa gtcgtttgga | 2650 |
| acaaaatatt ttttctttcc tggcagcttt taacattata gcaaatttgt | 2700 |
| gtctggggga ctgctggtca ctgtttctca cagttgcaaa tcaaggcatt | 2750 |
| tgcaaccaaa aaaaaaaaaa aaaaaatg | 2779 |

<210> SEQ ID NO 2
<211> LENGTH: 2273
<212> TYPE: DNA
<213> ORGANISM: Homo sapiens
<220> FEATURE:
<221> NAME/KEY: prim_transript
<223> OTHER INFORMATION: cDNA sequence of the short form of cytoplasmic polyadenylation element binding protein

<400> SEQUENCE: 2

| | |
|---|---|
| gacttccagg actctgaaga aacagttaca agcaggatgc ttttcccaac | 50 |

-continued

| | |
|---|---|
| ctctgcgcaa gaatcttccc gtggcctccc agatgcaaat gacttgtgcc | 100 |
| ttggcctgca gtccctcagt ctgacaggct gggaccgacc ctggagcacc | 150 |
| caggactcag attcctcagc ccagagcagc acacactcgg tactgagcat | 200 |
| gctccataac ccactgggaa atgtcctagg aaaacccccc ttgagcttcc | 250 |
| tgcctctgga tccccttggg tctgacttgg tggacaagtt ccagcaccc | 300 |
| tcagttagag gatcacgcct ggacacccgg cccatcctgg actctcgatc | 350 |
| tagcagcccc tctgactcag acaccagtgg cttcagctct ggatcagatc | 400 |
| atctctcaga tttgatttca agccttcgca tttctccacc tctgcccttc | 450 |
| ctgtctctgt caggggggtgg tcccagagac cctttaaaga tgggggtagg | 500 |
| gtctcggatg gaccaagagc aagctgctct tgctgcagtc actccctccc | 550 |
| caaccagtgc ttcaaagaga tggccaggag cttctgtgtg gccatcctgg | 600 |
| gacctcctcg aagctcccaa agaccccttc agcatagaga gagaggccag | 650 |
| gctgcaccga caagctgcag ctgtgaatga agccacctgt acctggagtg | 700 |
| gccagcttcc tccccggaac tataagaacc ccatctactc ttgcaaggtg | 750 |
| tttctaggag gtgttccttg ggatattaca gaagctggat tagttaacac | 800 |
| cttccgtgtt tttggctctt tgagtgtgga gtggcctggt aaggatggca | 850 |
| agcatcccg gtgtcctccc aaaggtaata tgcctaaagg gtatgtgtat | 900 |
| ctggtcttcg aactagagaa gtctgtccga tccttgcttc aggcttgctc | 950 |
| tcatgacccg ctgagcccag atggcctgag tgaatattat ttcaagatgt | 1000 |
| ccagccgaag gatgcgctgc aaggaggtgc aggtgatccc ctgggtatta | 1050 |
| gccgacagta actttgtccg gagcccatct cagaggcttg accccagcag | 1100 |
| gacggtgttt gtcggtgctc tgcatggaat gctaaatgct gaggccctgg | 1150 |
| cagccatctt gaacgaccta tttggtggag tggtgtatgc cgggattgac | 1200 |
| acagataagc acaagtatcc cattggttct ggtcgtgtga cttctcaataa | 1250 |
| ccaacggagt tacctgaaag cagtcagcgc tgcttttgtg gagatcaaaa | 1300 |
| ccaccaagtt cacaaagaag gttcagattg acccctacct agaagattct | 1350 |
| ctgtgtcata tctgcagttc tcagcctggt cctttcttct gtcgagatca | 1400 |
| ggtctgcttc aaatacttct gccggagctg ctggcactgg cggcacagca | 1450 |
| tggagggcct gcgccaccac agccccctga tgcggaacca aagaaccga | 1500 |
| gattccagct agaggagctg gccttgccca gtggcctgtg gcgcccaaag | 1550 |
| ctggcaggtc aggcaagcag cctgcaccac cctgccactg gcgaccaggg | 1600 |
| agctggcttc ccaaggacaa gggaaaattg tagtcacctt tgcacttgct | 1650 |
| gaatctgtct ttgtttctgc actaattaat gcacattgag tttttgtcagg | 1700 |
| ttttgttttc agggggtgta ccaagggcaa ggaccctctg gcttaccctc | 1750 |
| caagcgactc tgtagttttc ccagatttta gttcctcatt ttgcagatga | 1800 |
| aaagcgggga aaaaaaaaa aaaaaaaatt cctgaaggta ttgacacgga | 1850 |
| tgcctacacc taggtttatt tattaaaagc gcttttttac attccttgca | 1900 |
| atactgatgg tgatgatgcg caggtctcat tggttttcatt cttgcagttg | 1950 |
| ccatacagtg cctttccatt tatttaaccc ccacctgaac ggcataaact | 2000 |

-continued

| | |
|---|---|
| gagtgttcag ctggtgtttt ttactgtaaa caataaggag actttgctct | 2050 |
| tcatttaaac caaaatcata tttcatattt tacgctcgag ggtttttacc | 2100 |
| ggttcctttt tacactcctt aaaacagttt ttaagtcgtt tggaacaaaa | 2150 |
| tatttttct ttcctggcag cttttaacat tatagcaaat ttgtgtctgg | 2200 |
| gggactgctg gtcactgttt ctcacagttg caaatcaagg catttgcaac | 2250 |
| caaaaaaaaa aaaaaaaaaa atg | 2273 |

<210> SEQ ID NO 3
<211> LENGTH: 566
<212> TYPE: PRT
<213> ORGANISM: Homo sapiens
<220> FEATURE:
<221> NAME/KEY: VARSPLIC
<223> OTHER INFORMATION: sequence of the long form of cytoplasmic
      polyadenylation element binding protein

<400> SEQUENCE: 3

```
Met Ala Leu Ser Leu Glu Glu Glu Ala Gly Arg Ile Lys Asp Cys
              5                  10                  15

Trp Asp Asn Gln Glu Ala Pro Ala Leu Ser Thr Cys Ser Asn Ala
             20                  25                  30

Asn Ile Phe Arg Arg Ile Asn Ala Ile Leu Asp Asn Ser Leu Asp
             35                  40                  45

Phe Ser Arg Val Cys Thr Thr Pro Ile Asn Arg Gly Ile His Asp
             50                  55                  60

His Leu Pro Asp Phe Gln Asp Ser Glu Glu Thr Val Thr Ser Arg
             65                  70                  75

Met Leu Phe Pro Thr Ser Ala Gln Glu Ser Ser Arg Gly Leu Pro
             80                  85                  90

Asp Ala Asn Asp Leu Cys Leu Gly Leu Gln Ser Leu Ser Leu Thr
             95                 100                 105

Gly Trp Asp Arg Pro Trp Ser Thr Gln Asp Ser Asp Ser Ser Ala
            110                 115                 120

Gln Ser Ser Thr His Ser Val Leu Ser Met Leu His Asn Pro Leu
            125                 130                 135

Gly Asn Val Leu Gly Lys Pro Pro Leu Ser Phe Leu Pro Leu Asp
            140                 145                 150

Pro Leu Gly Ser Asp Leu Val Asp Lys Phe Pro Ala Pro Ser Val
            155                 160                 165

Arg Gly Ser Arg Leu Asp Thr Arg Pro Ile Leu Asp Ser Arg Ser
            170                 175                 180

Ser Ser Pro Ser Asp Ser Asp Thr Ser Gly Phe Ser Ser Gly Ser
            185                 190                 195

Asp His Leu Ser Asp Leu Ile Ser Ser Leu Arg Ile Ser Pro Pro
            200                 205                 210

Leu Pro Phe Leu Ser Leu Ser Gly Gly Gly Pro Arg Asp Pro Leu
            215                 220                 225

Lys Met Gly Val Gly Ser Arg Met Asp Gln Glu Gln Ala Ala Leu
            230                 235                 240

Ala Ala Val Thr Pro Ser Pro Thr Ser Ala Ser Lys Arg Trp Pro
            245                 250                 255

Gly Ala Ser Val Trp Pro Ser Trp Asp Leu Leu Glu Ala Pro Lys
            260                 265                 270

Asp Pro Phe Ser Ile Glu Arg Glu Ala Arg Leu His Arg Gln Ala
```

```
                    275                 280                 285
Ala Ala Val Asn Glu Ala Thr Cys Thr Trp Ser Gly Gln Leu Pro
                290                 295                 300
Pro Arg Asn Tyr Lys Asn Pro Ile Tyr Ser Cys Lys Val Phe Leu
                305                 310                 315
Gly Gly Val Pro Trp Asp Ile Thr Glu Ala Gly Leu Val Asn Thr
                320                 325                 330
Phe Arg Val Phe Gly Ser Leu Ser Val Glu Trp Pro Gly Lys Asp
                335                 340                 345
Gly Lys His Pro Arg Cys Pro Pro Lys Gly Asn Met Pro Lys Gly
                350                 355                 360
Tyr Val Tyr Leu Val Phe Glu Leu Glu Lys Ser Val Arg Ser Leu
                365                 370                 375
Leu Gln Ala Cys Ser His Asp Pro Leu Ser Pro Asp Gly Leu Ser
                380                 385                 390
Glu Tyr Tyr Phe Lys Met Ser Ser Arg Arg Met Arg Cys Lys Glu
                395                 400                 405
Val Gln Val Ile Pro Trp Val Leu Ala Asp Ser Asn Phe Val Arg
                410                 415                 420
Ser Pro Ser Gln Arg Leu Asp Pro Ser Arg Thr Val Phe Val Gly
                425                 430                 435
Ala Leu His Gly Met Leu Asn Ala Glu Ala Leu Ala Ala Ile Leu
                440                 445                 450
Asn Asp Leu Phe Gly Gly Val Val Tyr Ala Gly Ile Asp Thr Asp
                455                 460                 465
Lys His Lys Tyr Pro Ile Gly Ser Gly Arg Val Thr Phe Asn Asn
                470                 475                 480
Gln Arg Ser Tyr Leu Lys Ala Val Ser Ala Ala Phe Val Glu Ile
                485                 490                 495
Lys Thr Thr Lys Phe Thr Lys Lys Val Gln Ile Asp Pro Tyr Leu
                500                 505                 510
Glu Asp Ser Leu Cys His Ile Cys Ser Ser Gln Pro Gly Pro Phe
                515                 520                 525
Phe Cys Arg Asp Gln Val Cys Phe Lys Tyr Phe Cys Arg Ser Cys
                530                 535                 540
Trp His Trp Arg His Ser Met Glu Gly Leu Arg His His Ser Pro
                545                 550                 555
Leu Met Arg Asn Gln Lys Asn Arg Asp Ser Ser
                560                 565

<210> SEQ ID NO 4
<211> LENGTH: 503
<212> TYPE: PRT
<213> ORGANISM: Homo sapiens
<220> FEATURE:
<221> NAME/KEY: VARSPLIC
<223> OTHER INFORMATION: sequence of the short form of cytoplasmic
      polyadenylation element binding protein

<400> SEQUENCE: 4

Asp Phe Gln Asp Ser Glu Glu Thr Val Thr Ser Arg Met Leu Phe
                5                   10                  15
Pro Thr Ser Ala Gln Glu Ser Ser Arg Gly Leu Pro Asp Ala Asn
                20                  25                  30
Asp Leu Cys Leu Gly Leu Gln Ser Leu Ser Leu Thr Gly Trp Asp
                35                  40                  45
```

```
Arg Pro Trp Ser Thr Gln Asp Ser Asp Ser Ser Ala Gln Ser Ser
             50                  55                  60

Thr His Ser Val Leu Ser Met Leu His Asn Pro Leu Gly Asn Val
             65                  70                  75

Leu Gly Lys Pro Pro Leu Ser Phe Leu Pro Leu Asp Pro Leu Gly
             80                  85                  90

Ser Asp Leu Val Asp Lys Phe Pro Ala Pro Ser Val Arg Gly Ser
             95                 100                 105

Arg Leu Asp Thr Arg Pro Ile Leu Asp Ser Arg Ser Ser Ser Pro
            110                 115                 120

Ser Asp Ser Asp Thr Ser Gly Phe Ser Gly Ser Asp His Leu
            125                 130                 135

Ser Asp Leu Ile Ser Ser Leu Arg Ile Ser Pro Pro Leu Pro Phe
            140                 145                 150

Leu Ser Leu Ser Gly Gly Pro Arg Asp Pro Leu Lys Met Gly
            155                 160                 165

Val Gly Ser Arg Met Asp Gln Glu Gln Ala Ala Leu Ala Ala Val
            170                 175                 180

Thr Pro Ser Pro Thr Ser Ala Ser Lys Arg Trp Pro Gly Ala Ser
            185                 190                 195

Val Trp Pro Ser Trp Asp Leu Leu Glu Ala Pro Lys Asp Pro Phe
            200                 205                 210

Ser Ile Glu Arg Glu Ala Arg Leu His Arg Gln Ala Ala Ala Val
            215                 220                 225

Asn Glu Ala Thr Cys Thr Trp Ser Gly Gln Leu Pro Pro Arg Asn
            230                 235                 240

Tyr Lys Asn Pro Ile Tyr Ser Cys Lys Val Phe Leu Gly Gly Val
            245                 250                 255

Pro Trp Asp Ile Thr Glu Ala Gly Leu Val Asn Thr Phe Arg Val
            260                 265                 270

Phe Gly Ser Leu Ser Val Glu Trp Pro Gly Lys Asp Gly Lys His
            275                 280                 285

Pro Arg Cys Pro Pro Lys Gly Asn Met Pro Lys Gly Tyr Val Tyr
            290                 295                 300

Leu Val Phe Glu Leu Glu Lys Ser Val Arg Ser Leu Leu Gln Ala
            305                 310                 315

Cys Ser His Asp Pro Leu Ser Pro Asp Gly Leu Ser Glu Tyr Tyr
            320                 325                 330

Phe Lys Met Ser Ser Arg Arg Met Arg Cys Lys Glu Val Gln Val
            335                 340                 345

Ile Pro Trp Val Leu Ala Asp Ser Asn Phe Val Arg Ser Pro Ser
            350                 355                 360

Gln Arg Leu Asp Pro Ser Arg Thr Val Phe Val Gly Ala Leu His
            365                 370                 375

Gly Met Leu Asn Ala Glu Ala Leu Ala Ala Ile Leu Asn Asp Leu
            380                 385                 390

Phe Gly Gly Val Val Tyr Ala Gly Ile Asp Thr Asp Lys His Lys
            395                 400                 405

Tyr Pro Ile Gly Ser Gly Arg Val Thr Phe Asn Asn Gln Arg Ser
            410                 415                 420

Tyr Leu Lys Ala Val Ser Ala Ala Phe Val Glu Ile Lys Thr Thr
            425                 430                 435
```

```
        Lys Phe Thr Lys Lys Val Gln Ile Asp Pro Tyr Leu Glu Asp Ser
                        440                 445                 450

Leu Cys His Ile Cys Ser Ser Gln Pro Gly Pro Phe Phe Cys Arg
                        455                 460                 465

Asp Gln Val Cys Phe Lys Tyr Phe Cys Arg Ser Cys Trp His Trp
                        470                 475                 480

Arg His Ser Met Glu Gly Leu Arg His His Ser Pro Leu Met Arg
                        485                 490                 495

Asn Gln Lys Asn Arg Asp Ser Ser
                        500         503

<210> SEQ ID NO 5
<211> LENGTH: 21
<212> TYPE: DNA
<213> ORGANISM: Artificial Sequence
<220> FEATURE:
<221> NAME/KEY: primer_bind
<223> OTHER INFORMATION: (+) primer to amplify a 180 bp product for
      RT-PCR analysis of human cytoplasmic polyadenylation
      element binding protein expression in immature
      human oocytes

<400> SEQUENCE: 5 agatggggt agggtctcgg a                                              21

<210> SEQ ID NO 6
<211> LENGTH: 21
<212> TYPE: DNA
<213> ORGANISM: Artificial Sequence
<220> FEATURE:
<221> NAME/KEY: primer_bind
<223> OTHER INFORMATION: (-) primer to amplify a 180 bp product for
      RT-PCR analysis of human cytoplasmic polyadenylation
      element binding protein expression in immature
      human oocytes

<400> SEQUENCE: 6
gcagcttgtc ggtgcagcct g                                             21

<210> SEQ ID NO 7
<211> LENGTH: 20
<212> TYPE: DNA
<213> ORGANISM: Artificial Sequence
<220> FEATURE:
<221> NAME/KEY: primer_bind
<223> OTHER INFORMATION: (-) primer for hCPEBL

<400> SEQUENCE: 7
gcatcctgct tgtaactgtt                                               20

<210> SEQ ID NO 8
<211> LENGTH: 18
<212> TYPE: DNA
<213> ORGANISM: Artificial Sequence
<220> FEATURE:
<221> NAME/KEY: primer_bind
<223> OTHER INFORMATION: (-) primer for hCPEBS

<400> SEQUENCE: 8
ggactgcagg ccaaggca                                                 18

<210> SEQ ID NO 9
<211> LENGTH: 21
<212> TYPE: DNA
<213> ORGANISM: Artificial Sequence
<220> FEATURE:
```

```
<221> NAME/KEY: primer_bind
<223> OTHER INFORMATION: (+) primer for hCPEBL

<400> SEQUENCE: 9
ggaagaagaa gcaggaagga t                                              21

<210> SEQ ID NO 10
<211> LENGTH: 28
<212> TYPE: DNA
<213> ORGANISM: Artificial Sequence
<220> FEATURE:
<221> NAME/KEY: primer_bind
<223> OTHER INFORMATION: (+) primer for hCPEBS

<400> SEQUENCE: 10
gcggaattcc agcgggaagc atcagcag                                       28

<210> SEQ ID NO 11
<211> LENGTH: 30
<212> TYPE: DNA
<213> ORGANISM: Artificial Sequence
<220> FEATURE:
<221> NAME/KEY: primer_bind
<223> OTHER INFORMATION: a (+) primer designed to amplify the last 48
      nucleotides of the Mos 3' UTR from pGEM Mos 321 UTR

<400> SEQUENCE: 11
gcgggatcca ttccatatgt gaatatatag                                     30

<210> SEQ ID NO 12
<211> LENGTH: 20
<212> TYPE: DNA
<213> ORGANISM: Artificial Sequence
<220> FEATURE:
<221> NAME/KEY: primer_bind
<223> OTHER INFORMATION: T7 promoter primer

<400> SEQUENCE: 12
taatacgact cactataggg                                                20

<210> SEQ ID NO 13
<211> LENGTH: 36
<212> TYPE: DNA
<213> ORGANISM: Artificial Sequence
<220> FEATURE:
<221> NAME/KEY: primer_bind
<223> OTHER INFORMATION: (+) PCR primer to construct plasmid
      pGEM XeMos mut UTR

<400> SEQUENCE: 13
cgcggatccc ccgggcacta gtagccagga gttcat                              36

<210> SEQ ID NO 14
<211> LENGTH: 42
<212> TYPE: DNA
<213> ORGANISM: Artificial Sequence
<220> FEATURE:
<221> NAME/KEY: primer_bind
<223> OTHER INFORMATION: (-) PCR primer to construct plasmid
      pGEM XeMos mut UTR

<400> SEQUENCE: 14
cgtctagaca aatcaatttc tttattacca aactatatat tc                       42

<210> SEQ ID NO 15
<211> LENGTH: 25
<212> TYPE: DNA
```

```
<213> ORGANISM: Artificial Sequence
<220> FEATURE:
<221> NAME/KEY: primer_bind
<223> OTHER INFORMATION: hCPEB-specific reverse primer

<400> SEQUENCE: 15
ggggatccag aggcaggaag ctcaa                                          25

<210> SEQ ID NO 16
<211> LENGTH: 173
<212> TYPE: DNA
<213> ORGANISM: Homo sapiens
<220> FEATURE:
<221> NAME/KEY: exon
<223> OTHER INFORMATION: first non-coding exon of hCPEBS

<400> SEQUENCE: 16
ggcagcggga agcatcagca gcctgatcac atgctggccc agtctgtaat              50
gcagacggga tagggtgtg tgtgtgaggg gaggggcct gtatggcaac                100 tgctcttgcc ccagcgtccc caaaagtgca gaggcagcgg ctgcagcatc              150
cagccagctt ggatgtctgg cct                                           173
```